United States Patent
Stahmann et al.

(10) Patent No.: US 6,522,921 B2
(45) Date of Patent: Feb. 18, 2003

(54) SYSTEM AND METHOD FOR ELIMINATING CROSS-TALK DUE TO FAR-FIELD SIGNALS

(75) Inventors: Jeffrey E. Stahmann, Ramsey, MN (US); Rene H. Wentkowski, White Bear Lake, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/748,722

(22) Filed: Dec. 26, 2000

(65) Prior Publication Data

US 2002/0082650 A1 Jun. 27, 2002

(51) Int. Cl.⁷ .............................................. A61N 1/362
(52) U.S. Cl. ........................................................ 607/9
(58) Field of Search ....................................... 607/4–28

(56) References Cited

U.S. PATENT DOCUMENTS

| | | | |
|---|---|---|---|
| 4,343,311 A | 8/1982 | Markowitz | 128/419 PG |
| 4,354,497 A | 10/1982 | Kahn | 128/419 D |
| 4,686,989 A | 8/1987 | Smyth et al. | 128/419 PG |
| 4,779,617 A | 10/1988 | Whigham | 128/419 P |
| 4,928,688 A | 5/1990 | Mower | 128/419 PG |
| 4,974,589 A | 12/1990 | Sholder | 128/419 PG |
| 5,103,820 A | 4/1992 | Markowitz | 128/419 OPG |
| 5,123,412 A | 6/1992 | Betzold | 128/419 PG |
| 5,129,393 A | 7/1992 | Brumwell | 128/419 PG |
| 5,156,149 A | 10/1992 | Hudrlik | 128/419 PG |
| 5,174,289 A | 12/1992 | Cohen | 128/419 PG |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,514,161 A | 5/1996 | Limousin | 607/9 |
| 5,584,867 A | 12/1996 | Limousin et al. | 607/9 |
| 5,653,738 A | 8/1997 | Sholder | 607/14 |
| 5,674,259 A | 10/1997 | Gray | 607/20 |
| 5,797,970 A | 8/1998 | Pouvreau | 607/9 |
| 5,935,160 A | 8/1999 | Auricchio et al. | 607/122 |
| 5,941,830 A | 8/1999 | Williams | 600/509 |
| 6,148,234 A | * 11/2000 | Struble | |

* cited by examiner

*Primary Examiner*—Scott M. Getzow
(74) *Attorney, Agent, or Firm*—Schwegman, Lundberg, Woessner & Kluth, P.A.

(57) ABSTRACT

A method and system for reducing the effects of far-field signals in a cardiac rhythm management device. Such far-field signals can be produced by contralateral ventricular depolarization and can cause cross-talk between ventricular sensing channels.

25 Claims, 4 Drawing Sheets

SYSTEM AND METHOD FOR ELIMINATING CROSS-TALK DUE TO FAR-FIELD SIGNALS

FIELD OF THE INVENTION

This invention pertains to methods and systems for operating a cardiac rhythm management device in which both atria or both ventricles are sensed. In particular, the invention relates to a method and system for eliminating cross-talk due to far-field signals from a sensing channel.

BACKGROUND

Cardiac rhythm management devices are implantable devices that provide electrical stimulation to selected chambers of the heart (i.e., the atrium and/or ventricle) in order to treat disorders of cardiac rhythm. A pacemaker, for example, is a cardiac rhythm management device that paces the heart with timed pacing pulses. (As the term is used herein, a pacemaker is any cardiac rhythm management device with a pacing functionality regardless of any other functions it may perform such as cardioversion or defibrillation.)

The most common condition for which pacemakers are used is in the treatment of bradycardia, where the ventricular rate is too slow. Atrio-ventricular conduction defects (i.e., AV block) that are fixed or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy can also be used in the treatment of congestive heart failure (CHF), which is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Some CHF patients suffer from some degree of AV block or are chronotropically deficient such that their cardiac output can be improved with conventional bradycardia pacing. It has also been shown, however, that some CHF patients suffer from conduction defects (e.g., bundle branch blocks) such that their cardiac outputs can be increased by improving the synchronization of cardiac contractions with electrical stimulation. In order to treat these problems, cardiac rhythm management devices have been developed which provide pacing stimulation to one or more heart chambers in an attempt to improve the coordination of atrial and/or ventricular contractions, termed cardiac resynchronization therapy.

SUMMARY OF THE INVENTION

Cardiac rhythm management devices that deliver resynchronization pacing to a heart chamber and its contralateral counterpart utilize sensing channels for each chamber in order to control the delivery of paces and for diagnostic purposes. It is possible, however, to misinterpret a depolarization occurring in one chamber as a sense in the opposite chamber. When a depolarization occurring in one chamber produces a far-field signal which is sensed in the sensing channel of the opposite chamber, a form of cross-talk between the sensing channels results.

The present invention is a system and method for eliminating cross-talk due to far-field signals from a sensing channel in a cardiac rhythm management device in which sensing channels are provided for a first heart chamber and a second heart chamber contralateral to the first chamber. In accordance with the invention, a sensing channel is rendered refractory for a specified time interval in order to avoid sensing both a chamber depolarization and a far-field signal from the opposite chamber during the same cardiac cycle.

The invention may be incorporated into an exemplary device for delivering ventricular resynchronization therapy in which paces are delivered to one or both ventricles based upon ventricular senses from one ventricle. In one embodiment, the ventricles are paced based upon right ventricular senses, and the left ventricular sensing channel is rendered refractory after a first ventricular sense for a specified time period. In the case where the first ventricular sense is a far-field signal due to a right ventricular depolarization, a subsequently detected left ventricular depolarization occurring during the same cardiac cycle is thus ignored and not regarded as an additional left ventricular sense. In another embodiment, a right ventricular sense triggers a cross-chamber left ventricular refractory period. This prevents the left ventricular sensing channel from interpreting a far-field signal due to a right ventricular depolarization as a left ventricular sense.

DESCRIPTION OF THE INVENTION

The present invention relates to a method for eliminating cross-talk between sensing channels due to far-field signals in a cardiac rhythm management device configured for biatrial or biventricular sensing. In the exemplary embodiments described below, the invention is incorporated into a cardiac rhythm management device that delivers paces to one or both ventricles based upon right ventricular events.

1. Hardware Platform

Cardiac rhythm management devices are typically implanted subcutaneously on a patient's chest and have leads threaded intravenously into the heart to connect the device to electrodes used for sensing and pacing. A programmable electronic controller causes pacing pulses to be output in response to lapsed time intervals and sensed electrical activity (i.e., intrinsic heart beats not as a result of a pacing pulse). Intrinsic cardiac electrical activity is sensed by means of internal electrodes disposed near or within the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
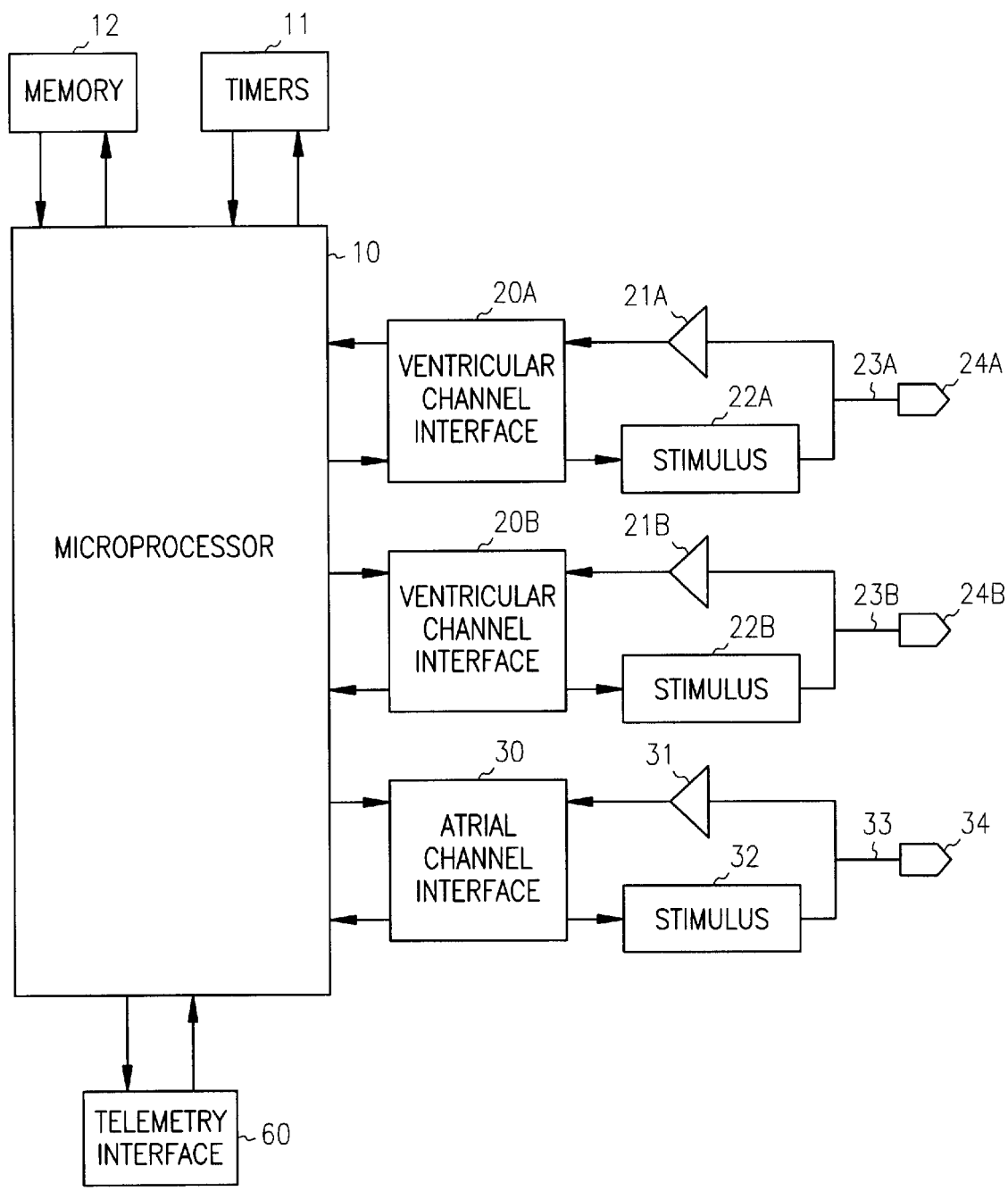
FIG. 1 is a system diagram of a pacemaker configured for biventricular pacing and sensing.

FIG. 1 shows a system diagram of a microprocessor-based cardiac rhythm management device physically configured with sensing and pacing channels for the atrium and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b where "a" designates one ventricular channel and "b" designates the other. In this embodiment, a single electrode is used for sensing and pacing, known as a unipolar lead. Other embodiments may employ bipolar leads which include two electrodes for outputting a pacing pulse and/or sensing intrinsic activity. The channel interfaces 20a–b and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. Also shown interfaced to the microprocessor 10 are a number of interval timers 11 which may either be discrete counters as shown or be implemented in software by the microprocessor executing programmed instructions in memory 12. A telemetry interface 60 is also provided for communicating with an external programmer. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, and implements timers for defining escape intervals and sensory refractory periods. It should be appreciated, however, that these functions could also be performed by custom logic circuitry either in addition to or instead of a programmed microprocessor.

2. Bradycardia Pacing Modes

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers, another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-triggered ventricular pacing attempts to maintain the atrio-ventricular synchrony occurring with physiological beats whereby atrial contractions augment diastolic filling of the ventricles. If a patient has a physiologically normal atrial rhythm, atrial-triggered pacing also allows the ventricular pacing rate to be responsive to the metabolic needs of the body. Atrial tracking modes are contraindicated when there is sinus node dysfunction or atrial fibrillation.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing, the lower rate interval is then the sum of the atrial escape interval and the atrio-ventricular interval.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. In a ventricular resynchronization pacing mode, for example, pacing stimulation is applied to one or both ventricles in a manner that improves the coordination of ventricular contractions. In delivering such therapy, it may be useful to pace only one ventricle on an inhibited demand basis in accordance with sense signals received from the opposite ventricle, pace one ventricle in a triggered mode in which an intrinsic beat in one ventricle triggers a pace in the opposite ventricle, pace both ventricles on an inhibited demand basis in accordance with sense signals received from only one ventricle, or pace both ventricles in a combination of triggered and inhibited demand modes. In the examples of resynchronization therapy that follow, ventricular pacing modes are based upon intrinsic activity in the right ventricle. It should be appreciated, however, that equivalent embodiments could be applied to ventricular resynchronization pacing modes based upon left ventricular intrinsic activity or to atrial resynchronization pacing.

One implementation of resynchronization therapy is biventricular (BV) pacing. In BV pacing, a left ventricular pace is delivered either simultaneously or in a timed relation with a right ventricle pace as specified by a biventricular offset interval. The offset interval may be zero in order to pace both ventricles simultaneously, positive in order to pace the left ventricle after the right, or negative if the left ventricle is paced before the right. In many cases, pumping efficiency of the heart will be increased by simultaneous pacing of the ventricles with an offset of zero. However, it may be desirable in certain patients to pace one ventricle before the other in order to compensate for different conduction velocities in the two ventricles, and this may be accomplished by specifying a particular biventricular offset interval. The ventricles may be paced on an inhibited demand basis where the ventricular escape interval is restarted with either a ventricular pace or a right ventricular sense. The pacing mode may also include atrial tracking. In that case, a pair of ventricular paces are delivered after expiration of the AVI escape interval or expiration of the LRL escape interval, with ventricular pacing inhibited by a right ventricular sense that restarts the LRL escape interval or stops the AVI escape interval. Since the ventricular escape interval in this mode is reset or stopped by senses only from the right ventricle, a left ventricular protection period may be provided that starts with the occurrence of a left ventricular sense and lasts for a specified time. A left ventricular pace is then not permitted upon expiration of the escape interval if it would occur within the protection period.

A variation of biventricular pacing is to pace only the left ventricle (LV-only pacing). LV-only pacing may be advantageous where the conduction velocities within the ventricles are such that pacing only the left ventricle results in a more coordinated contraction by the ventricles than with conventional right ventricular pacing or biventricular pacing. LV-only pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval or stops the AVI escape interval. As with BV pacing, a left ventricular pace may be inhibited if a left ventricular sense occurs within a protection period prior to expiration of the ventricular escape interval. Since an inhibited left ventricular pace in this mode could result in a cardiac cycle with no pacing, the mode may be further modified such that a right ventricular safety pace is delivered if the left ventricular pace is inhibited and no right ventricular sense has occurred.

Another form of resynchronization therapy is the delivery of pacing pulses to multiple sites of the same heart chamber. Certain pathologies may result in abnormal conduction of depolarization through the myocardium of a ventricle, for example, causing the ventricle to contract in an uncoordinated manner which hinders pumping action. Pacing pulses may be delivered to multiple sites in a specified time sequence during a cardiac cycle in an effort to produce a more effective ventricular contraction.

4. Elimination of Cross-talk due to Right Ventricular Far-Field Signals

A problem that arises when sensing depolarizations at a particular local cardiac site with a sensing channel dedicated to that site is the additional sensing of far-field signals from non-local sites. When sensing channels are provided for both atria or both ventricles, detection by a sensing channel dedicated to one chamber of far-field signals produced by the contralateral chamber produces a form of cross-talk between the sensing channels. This problem may be especially significant when unipolar leads are used for sensing depolarizations. With a unipolar lead, the signal fed to the sensing amplifier is the difference between the potential of the electrode attached to the lead and the potential of a reference electrode. The reference electrode may be, for example, either an electrode attached to another lead or the conductive housing of the implanted cardiac rhythm management device. In any case, the relatively wide spatial separation between the two electrodes makes the sensing channel for one heart chamber sensitive to depolarizations occurring in the opposite chamber (i.e., far-field signals). Cross-talk between the channels then occurs when a sensing channel detects a far-field signal due to contralateral depolarization and interprets it as a sense.

In a cardiac rhythm management device configured for biventricular resynchronization pacing based upon right ventricular senses as described above, cross-talk between the ventricular sensing channels caused by the sensing of right ventricular far-field signals by the left ventricular sensing channel can adversely affect the operation of the device in several ways. First, the left ventricular electrogram recorded by the device and displayed on an external programmer is corrupted with far-field data such that a left ventricular sense marker may represent a far-field signal instead of a true left ventricular depolarization, making the electrogram difficult to interpret. A measurement of the magnitude of a left ventricular R-wave may also be erroneous if the measurement is taken from a sensed far-field signal instead of a true left ventricular depolarization. Also, counts of ventricular senses and paces are generally maintained by cardiac rhythm management devices for diagnostic purposes and for display in the form of histograms on an external programmer. If both far-field signals (i.e., non-local) and true (i.e., local) left ventricular depolarizations are interpreted as left ventricular senses by the sensing channel, double counting of depolarization events occurs. Finally, in devices employing a left ventricular protection period, interpreting a far-field signal as a left ventricular sense results in premature triggering of the left ventricular protection period.

One means by which such undesirable cross-talk can be eliminated from the left ventricular sensing channel is to render the left ventricular sensing channel refractory for a specified time interval. In this manner, sensing both a far-field right ventricular signal and a left ventricular depolarization during the same cardiac cycle is avoided. A refractory period for a sensing channel is a time period during which sensed events are ignored by the device for purposes of diagnostic counting or for triggering or inhibiting paces.

Figure 2:
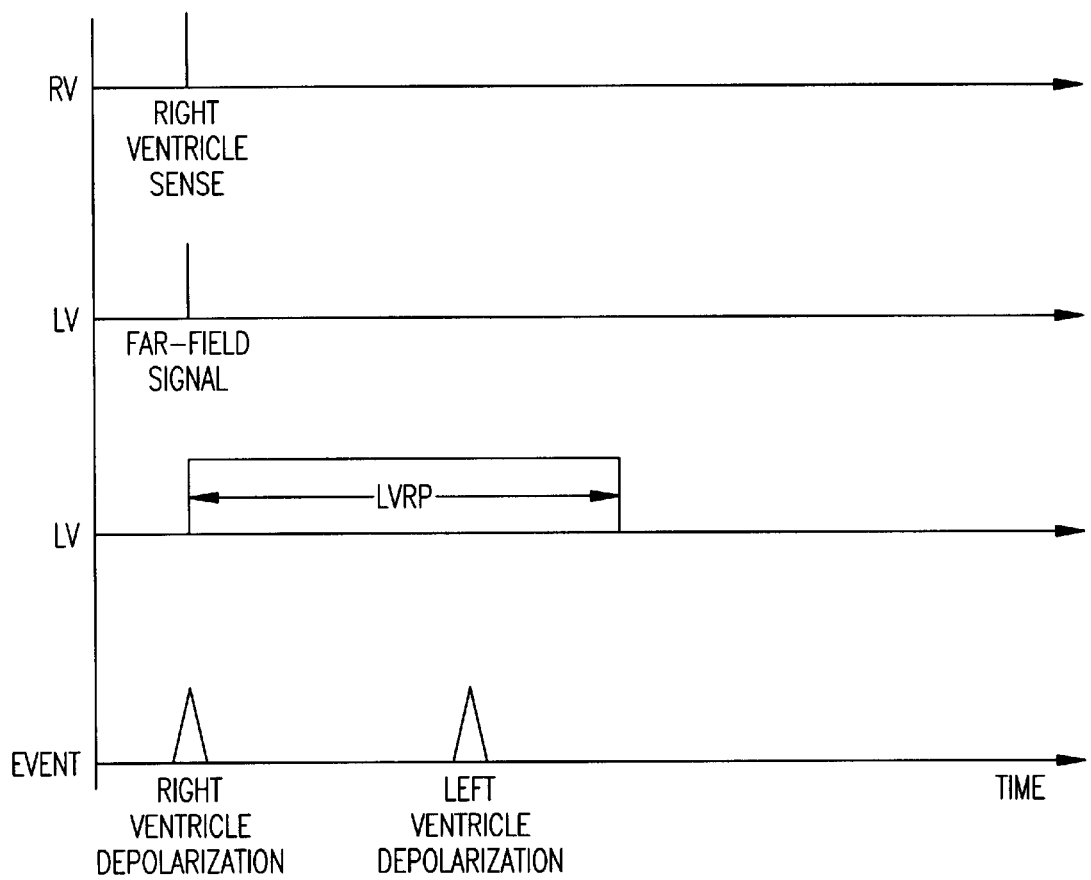
FIG. 2 illustrates a left ventricular refractory period triggered by a first ventricular sense.

In one embodiment, a left ventricular refractory period is triggered by a left ventricular sense during which further signals detected by the channel are ignored. The duration of the left ventricular refractory period would preferably be selected such that a muscle conducted left ventricular depolarization occurring after a right ventricular depolarization would occur within the triggered refractory period. In this manner, a far-field signal resulting from a right ventricular depolarization may be interpreted as a left ventricular sense by the left ventricular sensing channel for operational and diagnostic purposes. A subsequent true left ventricular depolarization falling within the triggered refractory period is then ignored, thus preventing double counting. FIG. 2 is a timing diagram showing events detected by the left ventricular sensing channel LV and the right ventricular sensing channel RV. A left ventricular refractory period LVRP is triggered by a right ventricular far-field signal detected by the left ventricular sensing channel. The subsequent true left ventricular depolarization is shown as falling within the refractory period LVRP.

As described above in the section dealing with ventricular resynchronization therapy, a left ventricular protection period may be provided for pacing modes based upon right ventricular events in order to prevent asynchronous pacing of the left ventricle. When a refractory period is provided for the left ventricular sensing channel, signals detected during this period are ignored, and the potential exists for delivery of a left ventricular pace coincident with an intrinsic depolarization. In the case of a left ventricular refractory period triggered by a left ventricular sense, for example, the refractory period may be triggered by a right ventricular depolarization detected as a far-field signal by the left ventricular sensing channel. A left ventricular depolarization occurring during the left ventricular refractive period will then fail to trigger the left ventricular protection period. The pacing algorithm is then free to deliver a left ventricular pace at the time of the intrinsic depolarization or shortly thereafter when the ventricle is vulnerable to induced fibrillation. In order to protect the left ventricle in this situation, the left ventricular protection period may be implemented so as to be triggered by depolarizations detected in the left ventricular sensing channel during both refractory and non-refractory periods.

Figure 3:
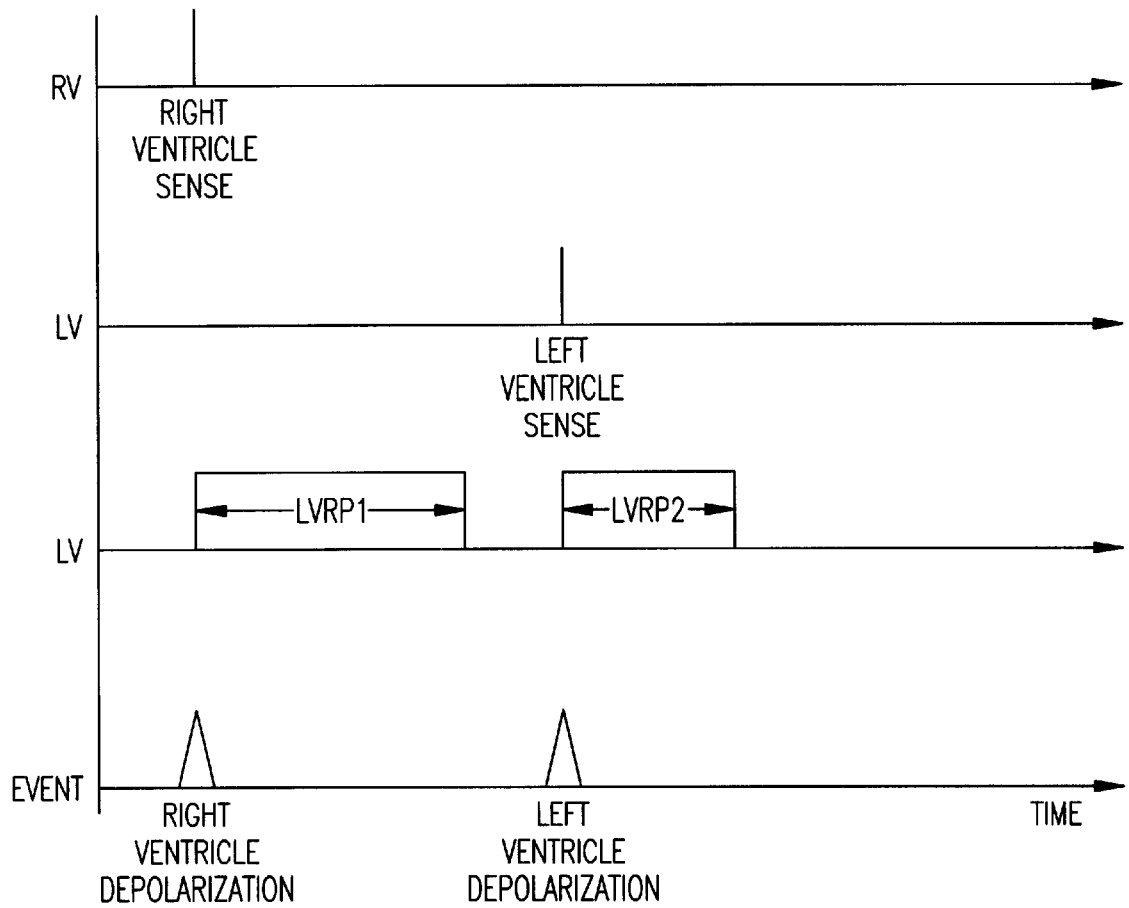
FIG. 3 illustrates a left ventricular refractory period triggered by a right ventricular sense.

In an alternative embodiment, a cross-chamber left ventricular refractory period triggered by a right ventricular sense is provided. FIG. 3 illustrates such a refractory period LVRP1 in the left ventricular sensing channel LV as triggered by a right ventricular sense. The refractory period LVRP1 in this embodiment thus prevents the far-field signal resulting from the right ventricular depolarization from being regarded as a left ventricular sense by the left ventricular sensing channel. The duration of the refractory period LVRP1 in this embodiment is preferably such that a subsequent true left ventricular depolarization falls outside of the refractory period and hence can be detected as a left ventricular sense. The true left ventricular sense triggers a same-chamber refractory period LVRP2, with LVRP1 and LVRP2 being independently programmable. As in the first embodiment described above, the left ventricular protection period may be triggered by refractory and non-refractory left ventricular senses. Alternatively, the left ventricular protection period may be implemented as a period triggered by either a left ventricular or a right ventricular sense. In that case, if a left ventricular depolarization occurs shortly after a right ventricular sense during the triggered left ventricular refractory period (and thus would not normally trigger the left ventricular protection period), the right ventricular sense provides the desired triggering of the left ventricular protection period.

Figure 4:
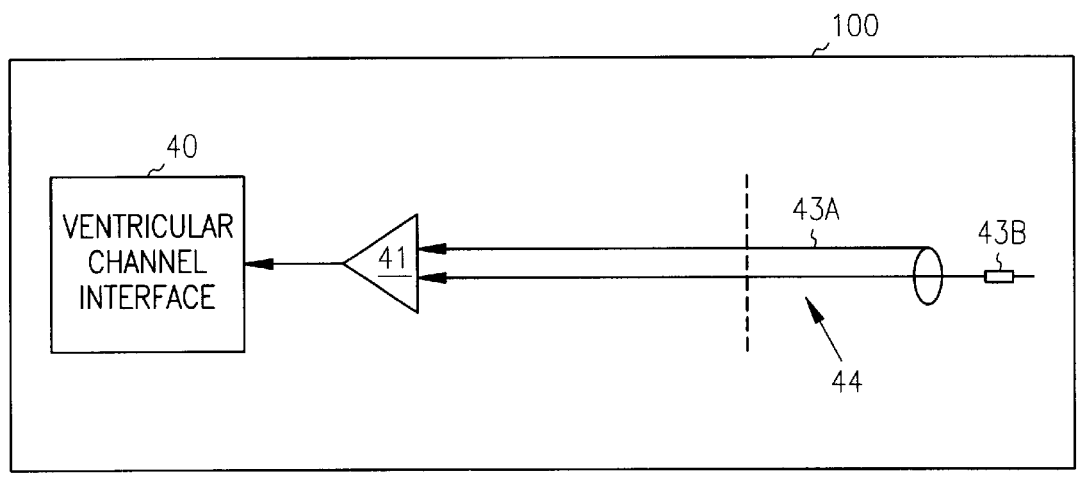
FIG. 4 shows a bipolar left ventricular sensing channel.

Another way to reduce cross-talk due to far-field signals is to reduce the sensitivity of the sensing channels to far-field signals. A bipolar lead, owing to the narrower spatial separation between the electrodes as compared with a unipolar lead, is less sensitive to far-field potentials. The use of a bipolar lead to sense the left ventricle thus results in reduced sensing of far-field signals due to right ventricular depolarization. FIG. 4 shows a left ventricular sensing channel within a device housing 100. A bipolar lead 44 includes a ring electrode 43a and a tip electrode 43b. The two electrodes are connected to a sensing amplifier 41 which is connected to a ventricular channel interface 40.

Figure 5:
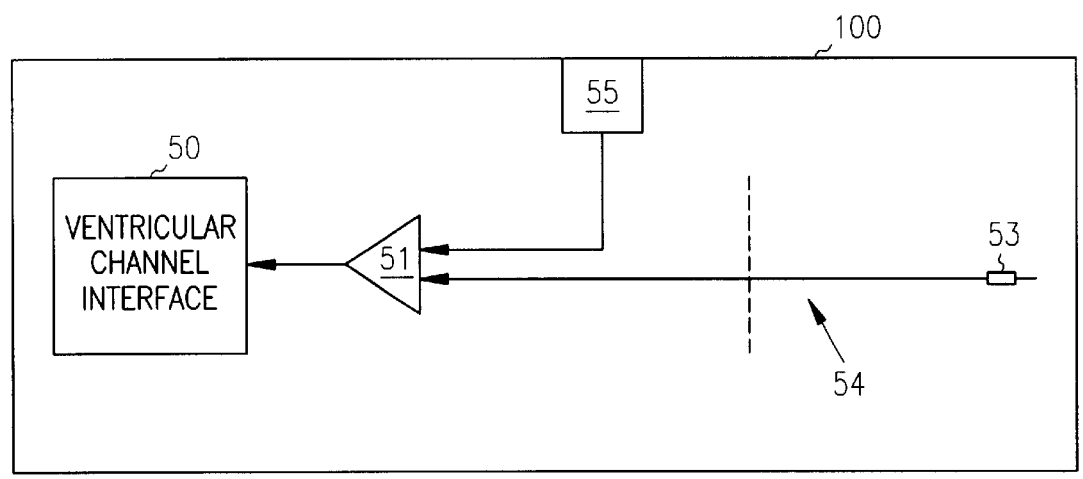
FIG. 5 shows a unipolar left ventricular sensing channel with the electrode referenced to a housing structure.

Certain biventricular pacing configurations employ a unipolar lead for sensing the left ventricle in which the electrode of the unipolar lead is referenced to an electrode of another lead. In this situation, a reduction in the sensitivity of the sensing channel to far-field potentials can be obtained by instead referencing the electrode of the unipolar lead to either the device housing or an electrode attached to a non-conductive part of the housing (e.g., the header of the device). FIG. 5 shows a left ventricular sensing channel that includes a channel interface 50 and a sensing amplifier 51. The electrode 53 of unipolar lead 54 is referenced to a housing structure 55, which represents either the conductive housing 100 itself serving as an electrode or a separate electrode attached to the device header.

The invention has been described above with reference to a cardiac rhythm management device configured to provide biventricular resynchronization therapy based upon right ventricular intrinsic activity. The invention may similarly be incorporated into devices that provide ventricular resynchronization therapy based upon left ventricular senses, that provide atrial resynchronization therapy, that provide resynchronization pacing to multiple sites of a single chamber, or that sense intrinsic cardiac activity through sensing channels for diagnostic purposes only and provide no pacing.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

sensing right and left ventricles through separate channels and generating ventricular sense signals upon detection of depolarization occurring in a ventricle;

pacing a ventricle upon expiration of a ventricular escape interval without receipt of a right ventricular sense signal from the right ventricle sensing channel;

rendering the left ventricular sensing channel refractory for a specified time interval in order to avoid sensing both a far-field right ventricular signal and a left ventricular depolarization during the same cardiac cycle.

2. The method of claim 1 wherein the left ventricular sensing channel is rendered refractory after a first ventricular sense for a specified time period.

3. The method of claim 2 wherein the left ventricle is paced upon expiration of a ventricular escape interval without receipt of a right ventricular sense signal from the right ventricle sensing channel, unless the pace would occur within a left ventricular protection period beginning after receipt of a left ventricular sense signal in which case no left ventricular pace is delivered; and, wherein the left ventricular protection period is triggered by a depolarization detected in the left ventricular sensing channel during both refractory and non-refractory periods.

4. The method of claim 1 wherein a right ventricular sense triggers a left ventricular refractory period.

5. The method of claim 1 wherein a left ventricular sense triggers a left ventricular refractory period.

6. The method of claim 4 wherein the left ventricle is paced upon expiration of a ventricular escape interval without receipt of a right ventricular sense signal from the right ventricle sensing channel, unless the pace would occur within a left ventricular protection period beginning after receipt of a left ventricular sense signal in which case no left ventricular pace is delivered; and, wherein the left ventricular protection period is triggered by a depolarization detected in the left ventricular sensing channel during both refractory and non-refractory periods.

7. The method of claim 4 wherein the left ventricle is paced upon expiration of a ventricular escape interval without receipt of a right ventricular sense signal from the right ventricle sensing channel, unless the pace would occur within a left ventricular protection period in which case no left ventricular pace is delivered; and, wherein the left ventricular protection period is triggered by either a left ventricular or a right ventricular sense.

8. A method for operating a cardiac rhythm management device, comprising:

sensing a first heart chamber and a second heart chamber contralateral to the first chamber through separate channels and generating separate sense signals upon detection of depolarization occurring in a chamber;

rendering a sensing channel refractory for a specified time interval in order to avoid sensing depolarizations from both chambers during the same cardiac cycle; and, wherein the first chamber is sensed with a bipolar lead in order to reduce the sensing of far-field signals due to depolarizations in the second chamber.

9. The method of claim 8 wherein the first and second chambers are the paired ventricles.

10. The method of claim 8 wherein the first and second chambers are the paired atria.

11. A method for operating a cardiac rhythm management device, comprising:

sensing a first heart chamber and a second heart chamber contralateral to the first chamber through separate channels and generating separate sense signals upon detection of depolarization occurring in a chamber;

rendering a sensing channel refractory for a specified time interval in order to avoid sensing depolarizations from both chambers during the same cardiac cycle; and, wherein the first chamber is sensed with a unipolar lead in which an electrode of the lead is referenced to a housing structure in order to reduce the sensing of far-field signals due to depolarizations in the second chamber.

12. The method of claim 11 wherein the first and second chambers are the paired ventricles.

13. The method of claim 11 wherein the first and second chambers are the paired atria.

14. The method of claim 11 wherein the housing structure is an electrode attached to a non-conductive part of a device housing.

15. A cardiac rhythm management device, comprising:

right and left ventricular sensing channels for sensing right and left ventricular depolarizations and generating ventricular sense signals in accordance therewith;

a pacing channel for delivering pacing pulses to a ventricle;

a controller for controlling the delivery of paces in accordance with a programmed pacing mode;

wherein the controller is programmed to render the left ventricular sensing channel refractory for a specified time interval in order to avoid sensing both a far-field right ventricular signal and a left ventricular depolarization during the same cardiac cycle.

16. The device of claim 15 wherein the left ventricular sensing channel is rendered refractory after a first ventricular sense for a specified time period.

17. The device of claim 16 wherein the controller is programmed to pace left ventricle upon expiration of a ventricular escape interval without receipt of a right ventricular sense signal from the right ventricle sensing channel, unless the pace would occur within a left ventricular protection period beginning after receipt of a left ventricular sense signal in which case no left ventricular pace is delivered; and, wherein the left ventricular protection period is triggered by a depolarization detected in the left ventricular sensing channel during both refractory and non-refractory periods.

18. The device of claim 15 wherein a right ventricular sense triggers a left ventricular refractory period.

19. The device of claim 18 wherein a left ventricular sense triggers a left ventricular refractory period.

20. The device of claim 18 wherein the controller is programmed to pace the left ventricle upon expiration of a ventricular escape interval without receipt of a right ventricular sense signal from the right ventricle sensing channel, unless the pace would occur within a left ventricular protection period beginning after receipt of a left ventricular sense signal in which case no left ventricular pace is delivered; and, wherein the left ventricular protection period is triggered by a depolarization detected in the left ventricular sensing channel during both refractory and non-refractory periods.

21. The device of claim 18 wherein the controller is programmed to pace the left ventricle upon expiration of a ventricular escape interval without receipt of a right ventricular sense signal from the right ventricle sensing channel, unless the pace would occur within a left ventricular protection period in which case no left ventricular pace is delivered; and, wherein the left ventricular protection period is triggered by either a left ventricular or a right ventricular sense.

22. A method for operating a cardiac rhythm management device, comprising:

sensing a first heart chamber and a contralateral second heart chamber through separate sensing channels; and, rendering a sensing channel refractory for a specified time interval in order to avoid sensing depolarizations from both chambers during the same cardiac cycle.

23. The method of claim 22 wherein the first and second heart chambers are the paired ventricles.

24. The method of claim 22 wherein the first and second heart chambers are the paired atria.

25. The method of claim 22 further comprising pacing a ventricle upon expiration of a ventricular escape interval without receipt of a right ventricular sense signal from a right ventricle sensing channel.

* * * * *